|   | United States Patent [19] | [11] | 4,442,089 |
|---|---|---|---|
|   | Horovitz | [45] | Apr. 10, 1984 |

[54] METHOD FOR TREATING GLAUCOMA WITH TOPICAL OR SYSTEMIC ACE INHIBITOR COMPOSITIONS

[75] Inventor: Zola P. Horovitz, Princeton, N.J.

[73] Assignee: E. R. Squibb & Sons, Inc., Princeton, N.J.

[21] Appl. No.: 395,542

[22] Filed: Jul. 6, 1982

[51] Int. Cl.³ .................. A61K 37/00; A61K 31/675; A61K 31/66; A61K 31/40

[52] U.S. Cl. .................................... 424/177; 424/200; 424/220; 424/274

[58] Field of Search ................ 424/177, 274, 220, 200

[56] References Cited

U.S. PATENT DOCUMENTS

| 3,711,602 | 1/1973 | Herschler | 424/45 |
|---|---|---|---|
| 3,873,618 | 3/1975 | Smith | 424/324 |
| 4,105,776 | 8/1978 | Ondetti et al. | 424/274 |
| 4,127,674 | 11/1978 | Leopold | 424/324 |
| 4,132,847 | 1/1979 | Kuhla et al. | 424/283 |
| 4,149,007 | 4/1979 | Buckler et al. | 562/463 |
| 4,152,450 | 5/1979 | Day et al. | 424/283 |
| 4,152,451 | 5/1979 | Archer et al. | 424/283 |
| 4,156,010 | 5/1979 | Hirschmann | 424/278 |
| 4,168,267 | 9/1979 | Petrillo | 424/274 |
| 4,179,517 | 12/1979 | Mechoulam et al. | 424/283 |
| 4,197,301 | 4/1980 | Smith et al. | 424/251 |

FOREIGN PATENT DOCUMENTS 12401 10/1979 European Pat. Off. .

OTHER PUBLICATIONS

Klin. Mbl. Augenheilk, 162 (1973), 637–642.
Biol. Abstr. vol. 71, 34826.
Biol. Abstr. vol. 72, 35289.
Biol. Abstr. vol. 71, 47987.

*Primary Examiner*—Delbert R. Phillips
*Attorney, Agent, or Firm*—Lawrence S. Levinson; Burton Rodney

[57] ABSTRACT

A method is provided for treating glaucoma by topical or systemic administration of an ACE inhibitor such as captopril.

14 Claims, No Drawings

METHOD FOR TREATING GLAUCOMA WITH TOPICAL OR SYSTEMIC ACE INHIBITOR COMPOSITIONS

FIELD OF THE INVENTION

The present invention relates to a method for treating glaucoma and/or of lowering intraocular pressure by topically or systemically administering an angiotensin converting enzyme inhibitor.

BACKGROUND OF THE INVENTION

U.S. Pat. No. 4,105,776 to Ondetti et al discloses proline derivatives which are angiotensin converting enzyme (ACE) inhibitors and have the general formula

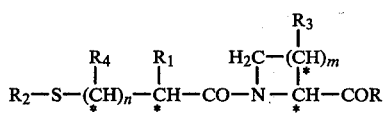

wherein

R is hydroxy, $NH_2$ or lower alkoxy;

$R_1$ and $R_4$ each is hydrogen, lower alkyl, phenyl or phenyl-lower alkyl;

$R_2$ is hydrogen, lower alkyl, phenyl, substituted phenyl wherein the phenyl substituent is halo, lower alkyl or lower alkoxy, phenyl-lower alkyl, diphenyl-lower alkyl, triphenyl-lower alkyl, lower alkylthiomethyl, phenyl-lower alkylthiomethyl, lower alkanoyl-amidomethyl,

$R_6$—S—, or $R_7$;

$R_3$ is hydrogen, hydroxy or lower alkyl;

$R_5$ is lower alkyl, phenyl or phenyl-lower alkyl;

$R_6$ is lower alkyl, phenyl, substituted phenyl (wherein the phenyl substituent is halo, lower alkyl or lower alkoxy), hydroxy-lower alkyl or amino(carboxy)-lower alkyl;

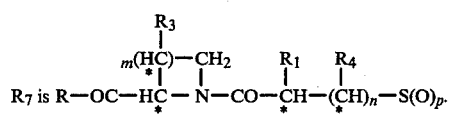

M is O or S;

m is 1 to 3;

n and p each is 0 to 2.

The asterisks indicate asymmetric carbon atoms. Each of the carbons bearing a substituent $R_1$, $R_3$ and $R_4$ is asymmetric when that substituent is other than hydrogen.

U.S. Pat. No. 4,168,267 to Petrillo discloses phosphinylalkanoyl prolines which have the formula

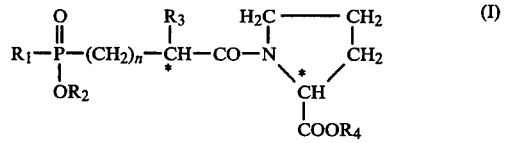

wherein $R_1$ is lower alkyl, phenyl or phenyl-lower alkyl;

$R_2$ is hydrogen, phenyl-lower alkyl or a metal ion;

$R_3$ is hydrogen or lower alkyl;

$R_4$ is hydrogen, lower alkyl, phenyl-lower alkyl or a metal ion; and n is 0 or 1.

U.S. application Ser. No. 212,911 to Petrillo filed Dec. 4, 1980 discloses phosphinylalkanoyl substituted prolines having the formula

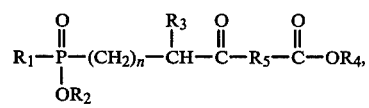

or a salt thereof, wherein $R_1$ is alkyl, aryl, arylalkyl, cycloalkyl, or cycloalkylalkyl;

one of $R_2$ and $R_4$ is

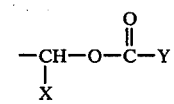

and the other is hydrogen, alkyl, arylalkyl or

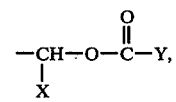

wherein X is hydrogen, alkyl or phenyl and Y is hydrogen, alkyl, phenyl or alkoxy, or together X and Y are —$(CH_2)_2$—, —$(CH_2)_3$—, —CH=CH— or

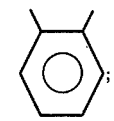

$R_3$ is hydrogen or alkyl;

—$R_5$—$COOR_4$ is

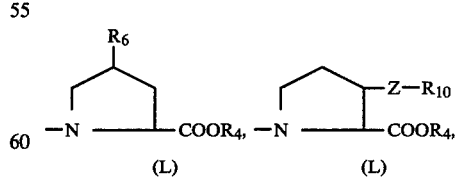

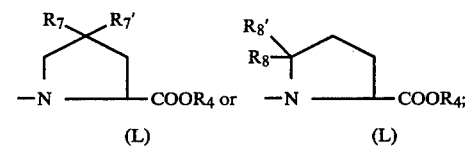

R6 is hydrogen, hydroxy, alkyl, halogen, azido, amino, cycloalkyl, aryl, arylalkyl, carbamoyloxy, N,N-dialkylcarbamoyloxy, or —Z—R9;

R7 and R'7 are the same and each is halogen or —Z—R10, or R7 and R'7 together are =O, —O—(CH2)m—O— or —S—(CH2)m—S—;

R8 is hydrogen and R'8 is phenyl, 2-hydroxyphenyl or 4-hydroxyphenyl or R8 and R'8 together are =O;

R9 is alkyl, aryl, arylalkyl, 1- or 2-naphthyl, or biphenyl;

R10 is alkyl, aryl or arylalkyl;

Z is oxygen or sulfur;

n is 0 or 1; and m is 1 or 2.

U.S. application Ser. No. 289,671 to Karanewsky et al, filed Aug. 3, 1981, discloses phosphonamidate substituted amino or imino acids which are angiotensin converting enzyme inhibitors and salts thereof and have the formula

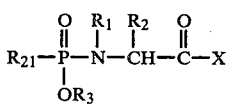

wherein X is an imino or amino acid of the formula

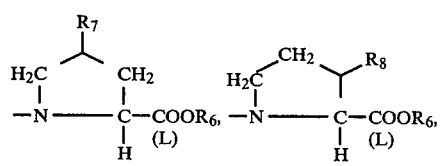

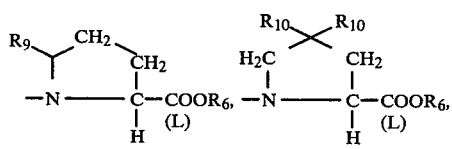

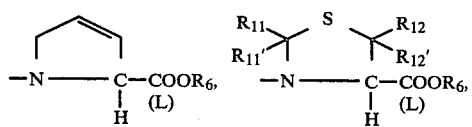

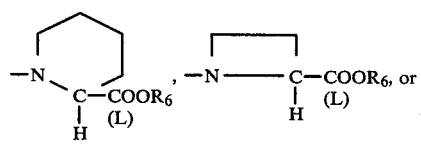

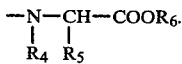

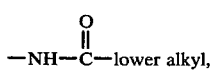

R7 is hydrogen, lower alkyl, halogen, keto, hydroxy, $$-NH-\overset{O}{\underset{}{C}}-\text{lower alkyl,}$$

azido, amino,

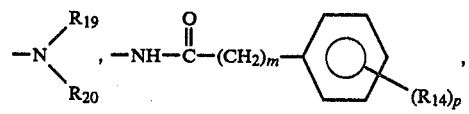

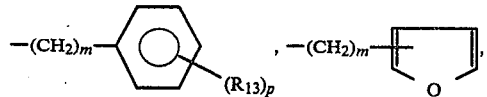

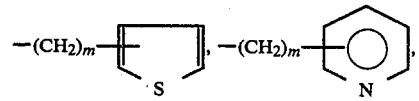

a 1- or 2-naphthyl of the formula

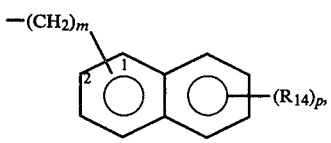

—(CH2)m—cycloalkyl,

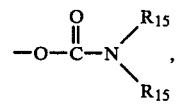

—O—lower alkyl,

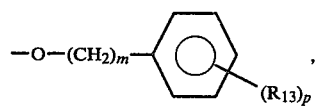

a 1- or 2-naphthyloxy of the formula

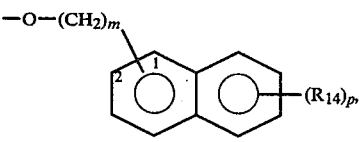

—S—lower alkyl,

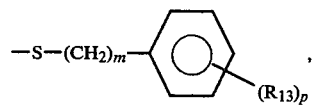

or a 1- or 2-naphthylthio of the formula

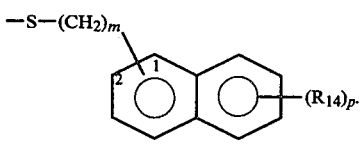

R8 is keto, halogen,

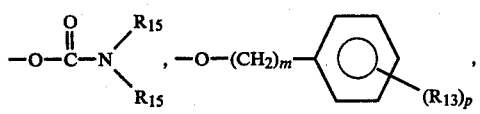

—O—lower alkyl, a 1- or 2-naphthyloxy of the formula

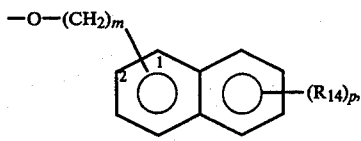

—S—lower alkyl,

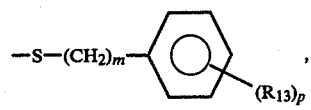

or a 1- or 2-naphthylthio of the formula

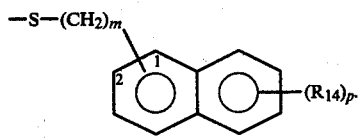

$R_9$ is keto or

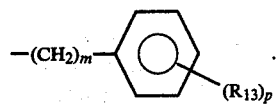

$R_{10}$ is halogen or —Y—$R_{16}$.
$R_{11}$, $R'_{11}$, $R_{12}$ and $R'_{12}$ are independently selected from hydrogen and lower alkyl or $R'_{11}$, $R_{12}$ and $R'_{12}$ are hydrogen and $R_{11}$ is

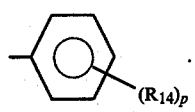

$R_{13}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl.
$R_{14}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy.
m is zero, one, two or three.
p is one, two or three provided that p is more than one only if $R_{13}$ or $R_{14}$ is hydrogen, methyl, methoxy, chloro, or fluoro.
$R_{15}$ is hydrogen or lower alkyl of 1 to 4 carbons.
Y is oxygen or sulfur.
$R_{16}$ is lower alkyl of 1 to 4 carbons,

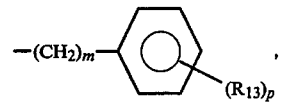

or the $R_{16}$ groups join to complete an unsubstituted 5- or 6-membered ring or said ring in which one or more of the carbons has a lower alkyl of 1 to 4 carbons or a di(lower alkyl of 1 to 4 carbons) substituent.
$R_4$ is hydrogen, lower alkyl, cycloalkyl, or

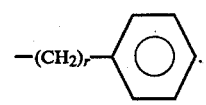

$R_5$ is hydrogen, lower alkyl,

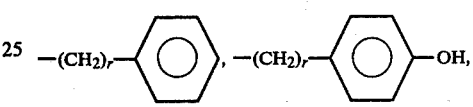

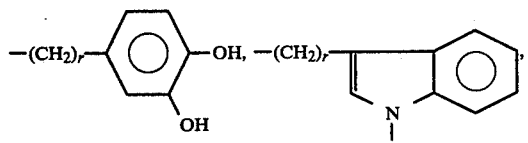

—$(CH_2)_r$—$NH_2$, —$(CH_2)_r$—SH, —$(CH_2)_r$—S— lower alkyl,

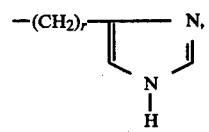

r is an integer from 1 to 4.
$R_1$ is hydrogen, lower alkyl, or cycloalkyl.
$R_2$ is hydrogen, lower alkyl, halo substituted lower alkyl,

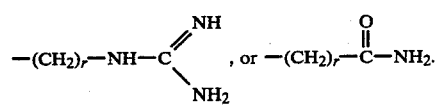

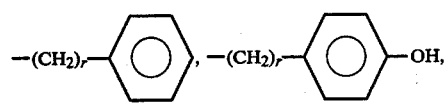

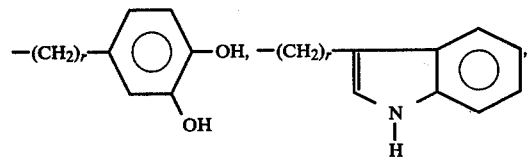

-continued

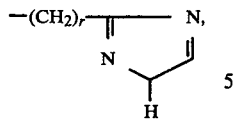

$-(CH_2)_r-NH_2$, $-(CH_2)_r-SH$, $-(CH_2)_r-S-$ lower alkyl,

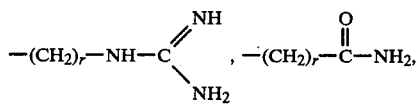

or $R_1$ and $R_2$ taken together are $-(CH_2)_n-$ wherein n is an integer from 2 to 4.

$R_3$ and $R_6$ are independently selected from hydrogen, lower alkyl, benzyl, benzhydryl, or

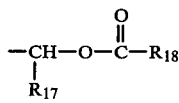

wherein $R_{17}$ is hydrogen, lower alkyl, or phenyl, and $R_{18}$ is hydrogen, lower alkyl, lower alkoxy, phenyl, or $R_{17}$ and $R_{18}$ taken together are $-(CH_2)_2-$, $-(CH_2)_3$, $-CH=CH$, or

$R_{19}$ is lower alkyl, benzyl, or phenethyl.
$R_{20}$ is hydrogen, lower alkyl, benzyl or phenethyl.
$R_{21}$ is alkyl of 1 to 10 carbons,

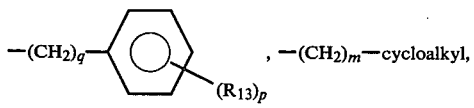

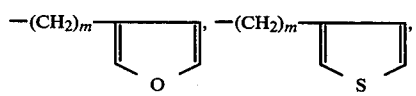

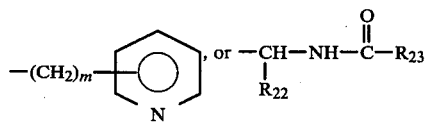

wherein q is zero or an integer from 1 to 7 and $R_{14}$, p and m are as defined above.

$R_{22}$ and $R_{23}$ are independently selected from hydrogen, lower alkyl, halo substituted lower alkyl,

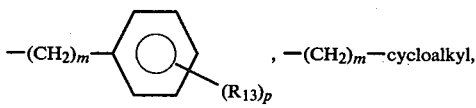

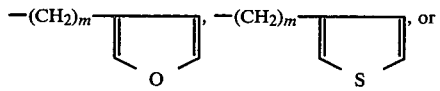

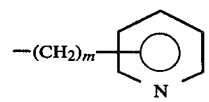

wherein m, $R_{14}$, and p are as defined above.

European Patent Application 0 012 401 published June 25, 1980 discloses carboxyalkyl dipeptide derivatives which are said to be angiotensin converting enzyme inhibitors and have the formula

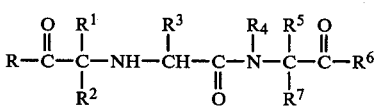

wherein
R and $R^6$ are the same or different and are hydroxy, lower alkoxy, lower alkenoxy, dilower alkylamino lower alkoxy (dimethylaminoethoxy), acylamino lower alkoxy (acetylaminoethoxy), acyloxy lower alkoxy (pivaloyloxymethoxy), aryloxy, such as phenoxy, arloweralkoxy, such as benzyloxy, substituted aryloxy or substituted arloweralkoxy wherein the substituent is methyl, halo or methoxy, amino, loweralkylamino, diloweralkylamino, hydroxyamino, arloweralkylamino such as benzylamino;

$R^1$ is hydrogen, alkyl of from 1 to 20 carbon atoms which include branched and cyclic and unsaturated (such as allyl) alkyl groups, substituted loweralkyl wherein the substituent can be halo, hydroxy, lower alkoxy, aryloxy such as phenoxy, amino, diloweralkylamino, acylamino, such as acetamido and benzamido, arylamino, guanidino, imidazolyl, indolyl, mercapto, loweralkylthio, arylthio such as phenylthio, carboxy or carboxamido, carboloweralkoxy, aryl such as phenyl or naphthyl, substituted aryl such as phenyl wherein the substituent is lower alkyl, lower alkoxy or halo, arloweralkyl, arloweralkenyl, heteroarlower alkyl or heteroarlower alkenyl such as benzyl, styryl or indolyl ethyl, substituted arloweralkyl, substituted arloweralkenyl, substituted heteroarlower alkyl, or substituted heteroarlower alkenyl, wherein the substituent(s) is halo, dihalo, lower alkyl, hydroxy, lower alkoxy, amino, aminomethyl, acylamino (acetylamino or benzoylamino) diloweralkylamino, loweralkylamino, carboxyl, haloloweralkyl, cyano or sulfonamido; arloweralkyl or heteroarloweralkyl substituted on the alkyl portion by amino or acylamino (acetylamino or benzoylamino);

$R^2$ and $R^7$ are the same or different and are hydrogen or lower alkyl;

$R^3$ is hydrogen, lower alkyl, phenyl lower alkyl, aminomethyl phenyl lower alkyl, hydroxy phenyl lower alkyl, hydroxy lower alkyl, acylamino lower alkyl (such as benzoylamino lower alkyl, acetylamino lower alkyl), amino lower alkyl, dimethylamino lower alkyl, halo lower alkyl, guanidino lower alkyl, imidazolyl lower alkyl, indolyl lower alkyl, mercapto lower alkyl, lower alkyl thio lower alkyl;

$R^4$ is hydrogen or lower alkyl;

$R^5$ is hydrogen, lower alkyl, phenyl, phenyl lower alkyl, hydroxy phenyl lower alkyl, hydroxy lower alkyl, amino lower alkyl, guanidino lower alkyl, imidazolyl lower alkyl, indolyl lower alkyl, mercapto lower alkyl or lower alkylthio lower alkyl;

$R^4$ and $R^5$ may be connected together to form an alkylene bridge of from 2 to 4 carbon atoms, an alkylene bridge of from 2 to 3 carbon atoms and one sulfur atom, an alkylene bridge of from 3 to 4 carbon atoms containing a double bond or an alkylene bridge as above substituted with hydroxy, loweralkoxy, lower alkyl or dilower alkyl;

and the pharmaceutically acceptable salts thereof.

Example 41 of the subject European Patent Application describes the preparation of N-(1-ethoxycarbonyl-3-phenylpropyl)-L-alanyl-L-proline.

DESCRIPTION OF THE INVENTION

In accordance with the present invention, a method is provided for treating glaucoma and/or of lowering intraocular pressure in mammalian species wherein a therapeutically effective amount of an angiotensin converting enzyme inhibitor is topically or is systemically, such as orally or parenterally, administered.

The angiotensin converting enzyme inhibitor which may be employed herein includes substituted proline derivatives, such as any of those disclosed in U.S. Pat. No. 4,105,776 to Ondetti et al mentioned above, with captopril, that is, 1-[(2S)-3-mercapto-2-methylpropionyl]-L-proline, being preferred, carboxyalkyl dipeptide derivatives, such as any of those disclosed in European Patent Application 0 012 401 mentioned above, with N-(1-ethoxycarbonyl-3-phenylpropyl)-L-alanyl-L-proline, that is

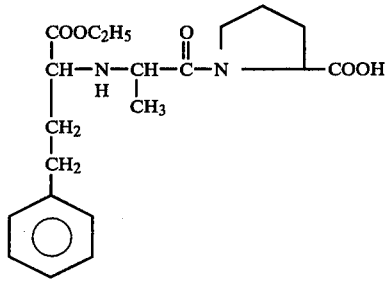

being preferred.

Other examples of angiotensin converting enzyme inhibitors suitable for use herein include any of the phosphinylalkanoyl prolines disclosed in U.S. Pat. No. 4,168,267 mentioned above, any of the phosphinylalkanoyl substituted prolines disclosed in U.S. application Ser. No. 212,911 discussed above, and the phosphonamidates disclosed in U.S. application Ser. No. 289,671 discussed above.

The disclosure of all of the above-mentioned U.S. patents and pending U.S. applications are incorporated herein by reference.

In carrying out the method of the present invention, the angiotensin converting enzyme inhibitor may be administered to mammalian species, such as monkeys, dogs, cats, rats, humans, etc. and as such may be incorporated in a conventional systemic dosage form, such as a tablet, capsule, elixir, injectable or a topical dosage form, such as sterile solutions, suspensions, ointments, powders for reconstitution or the like. The above dosage forms will also include the necessary carrier material, excipient, lubricant, buffer, antibacterial, bulking agent (such as mannitol), anti-oxidants (ascorbic acid or sodium bisulfite) or the like. Oral and topical dosage forms are preferred, although parenteral forms are quite satisfactory as well.

With regard to systemic formulations, single or divided doses of from about 8 to about 500 mg, preferably from about 20 to 100 mg/one to four times daily may be administered in systemic dosage forms as described above.

Topical compositions for use in carrying out the method of the invention are preferably solutions, ointments, or solid inserts. Such formulations may contain from 0.01 to 5% and especially 0.5 to 2% by weight of the ACE inhibitor. Higher dosages, for example about 10%, or lower dosages can be used provided the dose is effective in lowering intraocular pressure. As a unit dosage form from 0.001 to 5.0 mg, preferably 0.005 to 2.0 mg., and especially 0.005 to 1.0 mg. of the ACE inhibitor is generally applied to the human eye.

The topical carrier may conveniently be organic or inorganic. Typical pharmaceutically acceptable carriers include water containing a buffering agent, isotonic mixtures of water and water-miscible solvents, such as $C_{1-6}$ alkanols or aralkanols, vegetable oils, polyalkylene glycols, petroleum-based jelly, ethyl cellulose, ethyl oleate, carboxymethylcellulose, polyvinylpyrrolidone and isopropyl myristate. Among suitable buffering agents are sodium chloride, sodium borate, sodium phosphate, sodium acetate, and the gluconate buffers.

The topical preparation may also contain non-toxic auxiliary substances such as emulsifying, preserving, wetting and bodying agents, for example, polyethylene glycols 200, 300, 400, 600, 1,000, 1,500, 4,000, 6,000 and 10,000, bacterial components such as quaternary ammonium compounds, benzalkonium chloride, phenylmercuric salts known to have cold sterilizing properties and that are non-injurious in use, thimerosal, methyl and propyl paraben, benzyl alcohol, phenyl ethanol, sorbitan monolaurate, triethanolamine oleate, polyoxyethylene sorbitan monopalmitylate, dioctyl sodium sulfosuccinate, monothioglycerol, thiosorbitol and ethylenediamine tetracetic acid (chelating agent).

Additionally, suitable known topical ophthalmic vehicles can be used as carrier media for the present purpose including conventional phosphate buffer vehicle systems, isotonic boric acid vehicles, isotonic sodium chloride vehicles and isotonic sodium borate vehicles.

The topical preparation may also be in the form of a solid insert. For example, a solid water-soluble polymer may be used as the carrier for the ACE inhibitor. The polymer used to form the insert may be any water-soluble non-toxic polymer, for example, cellulose derivatives such as methylcellulose, sodium carboxymethyl cellulose; ($C_{1-6}$ hydroxyalkyl)cellulose such as hydroxyethyl cellulose, hydroxypropyl cellulose and hydroxypropylmethyl cellulose; acrylic acid derivatives such as polyacrylic acid salts, ethyl acrylates and polyacrylamides; natural products such as gelatin, alginates, pectins, tragacanth, karaya, chondrus, agar and acacia; the starch derivatives such as starch acetate, hydroxyethyl starch ethers, hydroxypropyl starch, and other synthetic derivatives such as polyvinyl alcohol, polyvinyl pyrrolidone, polyvinyl methyl ether, polyethylene oxide, neutralized carboxypolymethylene and xanthan gum, and mixtures of such polymers.

A complete description of solid inserts suitable for use herein is disclosed in British Patent Specification 1,524,405, which is incorporated herein by reference.

The following Examples represent preferred embodiments of the present invention.

EXAMPLE 1

A captopril formulation suitable for oral administration in the treatment of glaucoma is set out below.

1000 tablets each containing 100 mg of 1-[(2S)-3-mercapto-2-methylpropionyl]-L-proline are produced from the following ingredients:

| 1-[(2S)-3-Mercapto-2-methylpropionyl]-L-proline (captopril) | 100 g |
|---|---|
| Corn starch | 50 g |
| Gelatin | 7.5 g |
| Avicel (microcrystalline cellulose) | 25 g |
| Magnesium stearate | 2.5 g |

The captopril and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 100 mg of active ingredient which is used for treating glaucoma or reducing intraocular pressure.

EXAMPLE 2

By substituting 100 g of 1-(3-mercapto-2-D-methylpropanoyl)-L-proline for the captopril in Example 1, 1000 tablets each containing 100 mg of the 1-(3-mercapto-2-D-methylpropanoyl-L-proline are produced which is useful in treating glaucoma or reducing intraocular pressure.

EXAMPLE 3

1000 tablets each containing 200 mg of captopril are produced from the following ingredients:

| Captopril | 100 g |
|---|---|
| Lactose | 100 g |
| Avicel | 150 g |
| Corn starch | 50 g |
| Magnesium stearate | 5 g |

The captopril, lactose and Avicel are admixed, then blended with the corn starch. Magnesium stearate is added. The dry mixture is compressed in a tablet press to form 1000 505 mg tablets each containing 200 mg of active ingredient. The tablets are coated with a solution of Methocel E 15 (methyl cellulose) including as a color a lake containing yellow #6. The resulting tablets are useful in treating glaucoma or reducing intraocular pressure.

EXAMPLE 4

Two piece #1 gelatin capsules each containing 250 mg of captopril are filled with a mixture of the following ingredients:

| Captopril | 250 mg |
|---|---|
| Magnesium stearate | 7 mg |
| USP lactose | 193 mg |

The resulting capsules are useful in treating glaucoma or reducing intraocular pressure.

EXAMPLE 5

An injectable solution for use in treating glaucoma or in reducing intraocular pressure is produced as follows:

| Captopril | 500 mg |
|---|---|
| Methyl paraben | 5 g |
| Propyl paraben | 1 g |
| Sodium chloride | 25 g |
| Water for injection qs. | 5 l. |

The captopril, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains 5 ml of solution in a concentration of 100 mg of active ingredient per ml of solution for injection.

EXAMPLE 6

Tablets for use in treating glaucoma or in reducing intraocular pressure are prepared as described in Example 1 except that N-(1-ethoxycarbonyl-3-phenylpropyl)-L-alanyl-L-proline (MK421) is used in place of captopril.

EXAMPLE 7

An injectable for use in treating glaucoma or in reducing intraocular pressure is prepared as described in Example 5 except that N-(1-ethoxycarbonyl-3-phenylpropyl)-L-alanyl-L-proline (MK421) is employed in place of captopril.

EXAMPLE 8

A sterile solution for topical administration to the eye in treating glaucoma or reducing intraocular pressure is prepared as described below.

| Captopril | 1 mg | 15 mg |
|---|---|---|
| Sodium phosphate monobasic .2H$_2$O | 9.4 mg | 6.1 mg |
| Dibasic sodium phosphate .12H$_2$O | 28.5 mg | 16.8 mg |
| Benzalkonium chloride | 0.1 mg | 0.1 mg |
| Sodium hydroxide qs. | pH 6.8 | pH 6.8 |
| Water for injection qs ad | 1.0 ml | 1.0 mg |

Captopril, phosphate buffer salts, and benzalkonium chloride are added to and dissolved in water. The pH of the solution is adjusted to 6.8 with sodium hydroxide and the final solution diluted to volume. The solution is rendered sterile by filtration through a sterilizing filter.

EXAMPLE 9

A sterile solution for topically treating glaucoma or reducing intraocular pressure is prepared as described in Example 8 except that N-(1-ethoxycarbonyl-3-phenylpropyl)-L-alanyl-L-proline (MK421) is used in place of captopril.

EXAMPLE 10

Ophthalmic inserts containing captopril for use in treating glaucoma or reducing intraocular pressure is prepared as described below.

| | |
|---|---|
| Captopril | 1 mg |
| Hydroxypropylcellulose qs. | 12 mg |

Ophthalmic inserts are manufactured from compression molded films which are prepared on a Carver Press ('Carver' is a trademark) by subjecting the powder mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrated insert are then autoclaved at 250° F. for ½ hour.

EXAMPLE 11

Ophthalmic inserts for use in treating glaucoma are prepared as described below.

| | |
|---|---|
| N—(1-Ethoxycarbonyl-3-phenylpropyl)-L-alanyl-L-proline (MK421) | 1 mg |
| Hydroxypropyl cellulose qs ad. | 12 mg |

Ophthalmic inserts are manufactured from a solvent cast film prepared by making a viscous solution of the powder using methanol as the solvent. The solution is placed on a polytetrafluoroethylene plate and allowed to dry at ambient conditions. After drying, the film is placed in an 88% R.H. cabinet until it is pliable. Appropriately sized inserts are cut from the film.

EXAMPLE 12

Ophthalmic inserts for use in treating glaucoma are prepared as follows.

| | |
|---|---|
| 1-[N—[Hydroxy(4-phenylbutyl)-phosphinyl]-L-alanyl]-L-proline, disodium salt (prepared as described in U.S. application Ser. No. 289,671) | mg |
| Hydroxypropylmethyl cellulose qs. ad. | 12 mg |

Ophthalmic inserts are manufactured from a solvent cast film which is prepared by making a viscous solution of the powder blend using a methanol/water solvent system (10 ml methanol is added to 2.5 g of powder blend, to which 11 ml of water (in three divided portions) is added). The solution is placed on a polytetrafluoroethylene plate and allowed to dry under ambient conditions. After drying, the film is placed in an 88°/R.H. cabinet until it is pliable. Appropriately sized inserts are then cut from the film.

EXAMPLE 13

Ophthalmic inserts for use in treating glaucoma are prepared as follows.

| | |
|---|---|
| 1-[[Hydroxy(4-phenylbutyl)phosphinyl]-acetyl]-L-proline, (2,2-dimethyl-1-oxopropoxy)methyl ester (prepared as described in U.S. application Ser. No. 212,911) | 1 mg |
| Hydroxypropylmethyl cellulose qs ad. | 12 mg |

Ophthalmic inserts are manufactured from compression molded films which are prepared on a Carver Press by subjecting the powder mixture of the above ingredients to a compressional force of 12,000 lbs. (gauge) at 350° F. for one minute. The film is cooled under pressure by having cold water circulate in the platen. Ophthalmic inserts are then individually cut from the film with a punch. Each insert is placed into a vial, which is then placed in a humidity cabinet (88% R.H. at 30° C.) for two to four days. After removal from the humidity cabinet, the vials are stoppered and then capped. The vials containing the hydrated insert are then autoclaved at 250° F. for one-half hour.

EXAMPLE 14

Tablets for use in treating glaucoma or in reducing intraocular pressure are prepared as described in Example 1 except that 1-[N-[hydroxyl(4-phenylbutyl)phosphinyl]-L-alanyl]-L-proline, disodium salt (prepared as described in U.S. application Ser. No. 289,671) is used in place of captopril.

EXAMPLE 15

An injectable for use in treating glaucoma or in reducing intraocular pressure is prepared as described in Example 5 except that 1-[N-[hydroxy(4-phenylbutyl)-phosphinyl]-L-alanyl]-L-proline, disodium salt (prepared as described in U.S. application Ser. No. 289,671) is used in place of captopril.

EXAMPLE 16

A sterile solution for topical administration to the eye in treating glaucoma or reducing intraocular pressure is prepared as described below.

| | | |
|---|---|---|
| Captopril as 100% activity | | 5.25 mg/ml |
| Disodium edetate (EDTA) dihydrate | | 0.4 mg/ml |
| Sodium chloride | | 7.42 mg/ml |
| Sodium hydroxide | q.s. to | 4.5 pH (±0.1) |
| Hydrochloric acid | | |
| Water for injection | q.s. | 1.0 ml |

The water for injection is sparged with nitrogen. A portion of the water is added to the batching vessel. Thereafter, the disodium edetate and sodium chloride are added. The captopril is then added and the pH is adjusted with sodium hydroxide solution (e.g., 1.5 N) to pH 4.5±0.1 (final). All of the captopril must be in solution and small amounts of dilute hydrochloric acid may be used to back titrate, if necessary. Water for injection is then added to bring the formulation to proper volume.

The resulting sterile solution is useful in treating glaucoma or reducing intraocular pressure.

What is claimed is:

1. A method for treating glaucoma or lowering intraocular pressure in a mammalian species, which comprises topically or systemically administering an effective amount of an angiotensin converting enzyme inhibitor selected from the group consisting of a substituted proline derivative, a carboxyalkyl dipeptide derivative, a phosphinylalkanoyl proline derivative, and a phosphonamidate derivative.

2. The method as defined in claim 1 wherein said angiotensin converting enzyme inhibitor is administered orally or parenterally.

3. The method as defined in claim 1 wherein said angiotensin converting enzyme inhibitor is administered topically.

4. The method as defined in claim 1 wherein said angiotensin converting enzyme inhibitor is admixed with a pharmaceutically acceptable carrier therefor.

5. The method as defined in claim 1 wherein said angiotensin converting enzyme inhibitor is a substituted proline derivative.

6. The method as defined in claim 1 wherein said angiotensin converting enzyme inhibitor is a carboxyalkyl dipeptide derivative.

7. The method as defined in claim 1 wherein said angiotensin converting enzyme inhibitor is a phosphinylalkanoyl proline derivative.

8. The method as defined in claim 1 wherein said angiotensin converting enzyme inhibitor is a phosphonamidate derivative.

9. The method as defined in claim 1 wherein said angiotensin converting enzyme inhibitor is captopril.

10. The method as defined in claim 1 wherein said angiotensin converting enzyme inhibitor has the structure

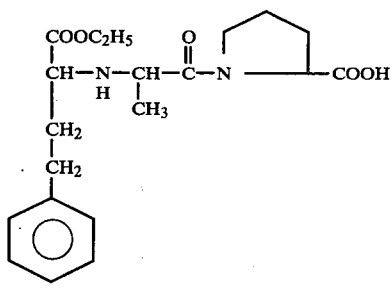

11. The method as defined in claim 1 wherein said angiotensin converting enzyme inhibitor is 1-[N-[hydroxy(4-phenylbutyl)phosphinyl]-2-alanyl]-L-proline or its disodium salt.

12. The method as defined in claim 1 wherein the angiotensin converting enzyme inhibitor is administered in the form of tablets, capsules, by injection or topically by sterile solution or ophthalmic insert.

13. The method as defined in claim 1 wherein the angiotensin converting enzyme inhibitor is captopril and is administered systemically in an amount of from about 8 to about 500 mg.

14. The method as defined in claim 1 wherein the angiotensin converting enzyme inhibitor is captopril and is administered topically in an amount of from about 0.001 to about 5 mg.

* * * * *

UNITED STATES PATENT AND TRADEMARK OFFICE
CERTIFICATE OF CORRECTION

PATENT NO. : 4,442,089
DATED : April 10, 1984
INVENTOR(S) : Zola P. Horovitz

It is certified that error appears in the above—identified patent and that said Letters Patent is hereby corrected as shown below:

Column 13, line 48, before "mg", insert --1--.

Signed and Sealed this

Twenty-third Day of October 1984

[SEAL]

Attest:

GERALD J. MOSSINGHOFF

Attesting Officer

Commissioner of Patents and Trademarks

Notice of Adverse Decision in Interference

In Interference No. 101,422, involving Patent No. 4,442,089, Z. P. Horovitz, METHOD FOR TREATING GLAUCOMA WITH TOPICAL OR SYSTEMIC ACE INHIBITOR COMPOSITIONS, final judgment adverse to the patentee, was rendered Mar. 12, 1986, as to claims 1-14.

[*Official Gazette June 17, 1986.*]